United States Patent [19]

Brannan et al.

[11] Patent Number: 5,211,947
[45] Date of Patent: May 18, 1993

[54] METHOD FOR LOWERING BLOOD CHOLESTEROL LEVELS WITH GRANULOCYTE-MACROPHAGE COLONY STIMULATING FACTOR

[75] Inventors: Melvin D. Brannan, Perkasie, Pa.; Hugh E. Black, Sparta, N.J.

[73] Assignee: Schering Corporation, Kenilworth, N.J.

[21] Appl. No.: 285,156

[22] Filed: Dec. 16, 1988

[51] Int. Cl.⁵ .................. A61K 37/547; A61K 45/05; A61K 37/02
[52] U.S. Cl. ............... 424/94.63; 424/94.64; 424/85.1; 514/166; 514/460; 514/568; 514/574; 514/824
[58] Field of Search ............... 424/94.64, 94.63, 85.1; 514/166, 568, 460, 574, 824

[56] References Cited

U.S. PATENT DOCUMENTS 4,788,183 11/1988 Darrow ........................... 514/166
5,019,381 5/1991 Garnick .......................... 424/85.1

FOREIGN PATENT DOCUMENTS 8703204 6/1987 PCT Int'l Appl. .

OTHER PUBLICATIONS

Tobert et al., Chem. Abstract, vol. 96:193161s (1982).
Watanabe et al., Chem. Abstracts, vol. 109:48144w (1988).
Leiss et al., Chem. Abstracts, vol. 102:197806w (1985).
Nimer et al., JAMA (Dec. 9, 1988) vol. 260, No. 22, pp. 3297-3300.
Verstraete et al., Blood (1986), vol. 67, No. 6, pp. 1529-1541.
Burgess and Metcalf, Blood, 56:947-958 (1980).
Metcalf, Blood, 67:257-267 (1986).
Brande et al., N. Engl. J. Med., 318:869-876 (1988).
Antman et al., New Engl. J. Med., 319:593-598 (1988).
Hancock et al., J. Immunol., 140:3021-3025 (1988).
Kurland et al., Proc. Natl. Acad. Sci. USA, 76:2326-2330 (1979).
Weisbart et al., Nature, 332:647-648 (1988).
Atkinson et al., Immunology, 64:519-525 (1988).
Coffey et al., J. Immunol. 140:2695-2701 (1988).

Primary Examiner—Jacqueline Stone
Attorney, Agent, or Firm—Norman C. Dulak

[57] ABSTRACT

A method for lowering the blood cholesterol levels in mammals and humans by administering GM-CSF is disclosed.

5 Claims, No Drawings

METHOD FOR LOWERING BLOOD CHOLESTEROL LEVELS WITH GRANULOCYTE-MACROPHAGE COLONY STIMULATING FACTOR

BACKGROUND OF THE INVENTION

This invention relates to the lowering of blood cholesterol levels in mammals and humans by administering a cholesterol lowering effective amount of granulocyte-macrophage colony stimulating factor (GM-CSF).

GM-CSF is a lymphokine (stimulator of the immune system) that exhibits a broad spectrum of immune cell stimulation as described in Burgess and Metcalf, *Blood*, 56: 947 (1980) and Metcalf, *Blood*, 67: 257 (1986). GM-CSF has been shown to increase the leukocyte count in patients with acquired immunodeficiency syndrome [Brandt et al., *N. Engl. J. Med.*, 318: 869 (1988)] and people suffering from chemotherapy-induced myelosuppression [Antman et al., *New Engl. J. Med.*, 319: 593 (1988)] and it has been suggested that various colony stimulating factors alone or in combination with erythropoietin and/or an antiviral agent and/or interleukin-2 (IL-2) may be useful for the treatment of patients suffering from AIDS-type disease (PCT Application No. 87/03204).

Although GM-CSF was identified because of its ability to stimulate proliferation of hematopoietic precursor cells, it is also able to stimulate a number of functional aspects of mature granulocytes and macrophages. These effects include synthesis of biologically active molecules such as prostaglandin E [Hancock et al., *J. Immunol.*, 140: 3021 (1988) and Kurland et al., *Proc. Natl. Acad. Sci. USA*, 76: 2326 (1979)]; increased phagocytic activity [Weisbart et al., *Nature*, 332: 647 (1988)]; expression and/or affinity of various membrane markers such as the IL-2 receptor [Hancock et al., *J. Immunol.*, 140: 3021 (1988)] and the bacterial product formylmethionylleucylphenylalanine receptor on neutrophils, which receptors elicit the production of superoxide anions [Atkinson et al., *Immunology*, 64: 519 (1988)]; and the regulation of enzyme activity such as the stimulation of guanylate cyclase and the inhibition of adenylate cyclase [Coffey et al., *J. Immunol.*, 140: 2695 (1988)].

SUMMARY OF THE INVENTION

The method of this invention involves administering to mammals, including humans, a serum cholesterol lowering effective amount of GM-CSF. Preferably, the GM-CSF is administered to mammals diagnosed as having elevated blood serum cholesterol levels (hypercholesterolemia).

Preferably, the mammals treated will be humans and the GM-CSF utilized will be one of the human allotypes.

In one embodiment, the GM-CSF will be administered by intravenous injection or intravenous infusion. Preferably, the GM-CSF will be administered in an amount of about 1 to about 600 micrograms per kilogram of body weight per day, more preferably about 1 to about 30 micrograms per kilogram of body weight per day, more preferably about 3 to about 30 micrograms per kilogram of body weight per day, and most preferably about 10 to about 30 micrograms per kilogram of body weight per day.

DETAILED DESCRIPTION OF THE INVENTION

The invention provides a method for lowering blood cholesterol levels in mammals, e.g,. mammals with hypercholesterolemia, by administering a serum cholesterol lowering effective amount of GM-CSF. Elevated cholesterol levels can be associated with cardiovascular disease (e.g. atherosclerosis) and hypertension.

Any suitable GM-CSF may be employed in the present invention. Complementary DNAs (cDNAs) for GM-CSF have recently been cloned and sequenced by a number of laboratories, e.g. Gough et al., *Nature*, 309: 763 (1984) (mouse); Lee et al., *Proc. Natl. Acad. Sci. USA*, 82: 4360 (1985) (human); Wong et al., *Science*, 228: 810 (1985) (human and gibbon); Cantrell et al., *Proc. Natl. Acad. Sci. USA*, 82: 6250 (1985) (human). Moreover, non-recombinant GM-CSF has been purified from various culture supernatants, e.g. Burgers et al., *Exp. Hematol.*, 9: 893 (1981) (mouse); Sparrow et al., *Exp. Hematol.*, 12: 267 (1984) (rat); Gasson et al., *Science*, 230: 1171 (1985) (human); Burgess et al., *Blood*, 69: 43 (1987) (human). Among the human GM-CSFs, nucleotide sequence and amino acid sequence heterogeneity have been observed. For example, both threonine and isoleucine have been observed at position 100 of human GM-CSF with respect to the N-terminal alanine, suggesting that allelic forms, or polymorphs, of GM-CSF may exist within human populations. Also, various leader sequences may occur at the N-terminal position of the amino acid sequence. These leader sequences may be of various lengths and amino acid composition, which may or may not affect biological activity. Preferably, the GM-CSF used in the present invention for treating humans will be a human GM-CSF (hGM-CSF), most preferably the GM-CSF described in Lee et al., *Proc. Natl. Acad. Sci. USA*, 82: 4360 (1985), as purified in U.S. patent application Ser. No. 111,886, filed Oct. 23, 1987. All of the above discussed references are incorporated herein by reference for their disclosures of representative GM-CSFs suitable for use in the present invention including their DNA and amino acid sequences and for their disclosures of methods for producing and purifying GM-CSF.

According to this invention, mammals are administered a serum cholesterol lowering effective amount of a GM-CSF. A serum cholesterol lowering effective amount is defined as any amount that will significantly lower the cholesterol level. A lowering of cholesterol by at least 5 percent is considered significant. From about 3 to about 30 micrograms of GM-CSF, preferably hGM-CSF, per kilogram of body weight per day is preferably administered. More preferably, hypercholesterolemic mammals are administered about 10 to about 30 micrograms of hGM-CSF per kilogram of body weight per day.

The amount, frequency and period of administration will vary depending upon factors such as the cholesterol level, (e.g. severity of the cholesterol elevation), age of the patient, nutrition, etc. Usually, the administration will be daily initially and it may continue periodically during the patient's lifetime. Dosage amount and frequency may be determined during initial screenings of cholesterol levels and the magnitude of the effect of GM-CSF upon the lowering of the cholesterol levels. Dosage will be aimed to lower the cholesterol level to an acceptable level of about 240 milligrams per deciliter of blood serum, preferably about 200 milligrams per deciliter of blood serum.

To complement the cholesterol lowering effect of GM-CSF, it may be useful to administer it in conjunction with other pharmaceutically active compounds. For example, it can be combined with other cholesterol lowering agents [e.g., lovastatin (1,2,3,7,8,8a-hexahydro-3,7-dimethyl-8-[2-(tetrahydro-4-hydroxy-6-oxo-2H-pyran-2-yl)-ethyl]-1-naphthalenyl 2-methylbutanoate, (U.S. Pat. No. 4,231,938)) available from Merck, Inc., Rahway, NJ; gemfribrozil (5-(2,5-dimethylphenoxy)-2,2-dimethylpentanoic acid), available from Parke-Davis, Inc., Ann Arbor, Mich.; dilevalol (5-{1-hydroxy-2-[(1-methyl-3-phenylpropyl)amino]ethyl} salicylamide (U.S. Pat. No. 4,788,183)); and pravastatin, which is available from Squibb, Inc., Princeton, N.J.]. For lowering cholesterol levels that may be associated with acute manifestations of heart disease such as myocardial infarction, GM-CSF can be administered in conjunction with thrombolytic agents [e.g., tissue plasminogen activators (tPAs) (for example, those disclosed in U.S. Pat. Nos. 4,370,417, 4,752,603; U.K. Patent No. 2,119,804; PCT Patent Application Nos. 87/05934, 87/04722, 84/01786; Australian Patent Application No. 55514/86; EPO Patent Application Nos. 227,462, 234,051, 238,304, and 174,835, and the tPA is commercially available from Genentech, Inc., South San Francisco, Calif.; eminase (anisoylated plasminogen streptokinase activator complex available from Beecham Inc., Bristol, Tenn., and Upjohn Corporation, Kalamazoo, Mich.); and streptokinase (for example, the materials disclosed in European Patent Application Nos. 248,227, 28,489; and the streptokinase commercially available from Burroughs-Wellcome, Inc., Research Triangle, N.C.)] or combinations of such thrombolytic agents (for example, see European Patent Application Nos. 91,240 and 28,489 for streptokinase/tPA complexes). These references are hereby incorporated by reference to illustrate examples of other cholesterol lowering agents and thrombolytic agents that can be used in combination with GM-CSF in certain embodiments of the present invention. The specific cholesterol lowering agents and thrombolytic agents mentioned above are merely examples of such agents known to those skilled in the art that can be used in the practice of the present invention.

Administration of the dose can be intravenous, nasal, parenteral, oral, subcutaneous, intramuscular, topical, transdermal or any other acceptable method. The GM-CSF could be administered in any number of conventional dosage forms. Parenteral preparations include sterile solutions or suspensions. Inhalation administration can be in the form of a nasal or oral spray, or by insufflation. Topical dosage forms can be creams, ointments, lotions, transdermal devices (e.g., of the conventional resevoir or matrix patch type) and the like.

The formulations and pharmaceutical compositions contemplated by the above dosage forms can be prepared with conventional pharmaceutically acceptable excipients and additives, using conventional techniques.

Presently, the GM-CSF is administered via the intravenous route. The solutions to be administered may be reconstituted from lyophilized powders and they may additionally contain preservatives, buffers, dispersants, etc. Preferably, GM-CSF is reconstituted with any isotonic medium normally utilized for intravenous injection, e.g., preservative-free sterile water. The maximum concentration of GM-CSF preferably should not exceed 1500 micrograms per milliliter. Administration may be accomplished by continuous intravenous infusion or by intravenous injection. For continuous infusion, the daily dose can be added to normal saline and the solution infused by mechanical pump or by gravity.

The effect of GM-CSF on lowering the serum cholesterol levels in monkeys and humans can be determined by the following test protocols:

Monkeys

Cynomolgus monkeys (*Macaca fascicularis*) are administered hGM-CSF, which is obtained as described in Lee et al., *Proc. Natl. Acad. Sci.* USA, 82: 4360 (1985) and U.S. patent application Ser. No. 111,886, filed Oct. 23, 1987. The route of administering the hGM-CSF is by intravenous injection in the saphenous vein for about 15 seconds and dosing occurrs daily. Blood samples are taken at the times indicated in the following tables by femoral venipuncture following an overnight fast. Blood samples are taken at two times prior to dosing with the hGM-CSF ($-2$ and $-1$ weeks prior to initial GM-CSF dosing) and control animals (receiving GM-CSF doses of 0.0 mg/kg/day in Table 1) are maintained that never received any dose of the hGM-CSF. The blood samples can be assayed for blood cholesterol levels using an enzymatic DACOS analyzer which is commercially available from Coulter Electronics, Inc., 600 West 20 Street, Hialeah, FL 33010.

Taking the averages for the various doses in Table 1 resulted in percent lowering of cholesterol levels of 8% at 0.03 mg/kg dose, 14% at 0.09 mg/kg dose, and 27% at 0.30 mg/kg dose.

Humans

Human subjects are given 10 equal daily doses of the hGM-CSF described above. The administration is by intravenous infusion over a 30 minute time period. Blood samples are collected at several times during the 10 day administration period and analyzed for blood cholesterol levels using the same procedure as that used above. The cholesterol levels for each subject are compared to baseline (the cholesterol level determined prior to administering the GM-CSF) and the percent decrease in cholesterol levels is calculated. The maximum decrease for each patient is selected and tabulated and the median maximum percent decrease in cholesterol for each dose is determined. The median maximum percent decrease in cholesterol levels is the middle value, such that half the values for a particular dose lie above and half lie below the median. Table 2 and Table 3 show such median maximum percent decreases in cholesterol levels by dose for two different patient populations.

TABLE 1

| Cholesterol Lowering Effect of GM-CSF in Monkeys | | | | |
|---|---|---|---|---|
| | GM-CSF Dose | Week of Dosing[a] | | |
| Animal No. | (mg/kg/day) | −2 | −1 | 4 | +4[b] |
| 1(M) | 0.0 | 222 | 219 | 201 | |
| 5(M) | 0.0 | 210 | 212 | 183 | 180 |
| 19(M) | 0.0 | 93 | 87 | 101 | 108 |
| 25(M) | 0.0 | 113 | 121 | 100 | |
| 34(M) | 0.0 | 171 | 134 | 127 | |
| 6(F) | 0.0 | 130 | 144 | 160 | |
| 7(F) | 0.0 | 205 | 179 | 193 | |
| 8(F) | 0.0 | 167 | 152 | 166 | |
| 9(F) | 0.0 | 183 | 177 | 201 | 178 |
| 10(F) | 0.0 | 172 | 156 | 183 | 186 |
| 11(M) | 0.03 | 162 | 159 | 179 | |
| 12(M) | 0.03 | 142 | 124 | 103 | |

TABLE 1-continued

Cholesterol Lowering Effect of GM-CSF in Monkeys

| Animal No. | GM-CSF Dose (mg/kg/day) | Week of Dosing[a] | | | |
|---|---|---|---|---|---|
| | | −2 | −1 | 4 | +4[b] |
| 13(M) | 0.03 | 167 | 172 | 144 | |
| 14(F) | 0.03 | 146 | 147 | 148 | |
| 16(F) | 0.03 | 177 | 164 | 138 | |
| 38(F) | 0.03 | 178 | 188 | 182 | |
| 4(M) | 0.09 | 139 | 130 | 114 | |
| 17(M) | 0.09 | 116 | 139 | 106 | |
| 18(M) | 0.09 | 145 | 124 | 116 | |
| 41(M) | 0.09 | 107 | 138 | 96 | |
| 20(F) | 0.09 | 192 | 201 | 176 | |
| 22(F) | 0.09 | 193 | 169 | 122 | |
| 35(F) | 0.09 | 272 | 216 | 105 | |
| 2(M) | 0.30 | 124 | 118 | 270 | 124 |
| 3(M) | 0.30 | 133 | 120 | 74 | |
| 23(M) | 0.30 | 133 | 139 | 70 | |
| 26(M) | 0.30 | 128 | 133 | 94 | 103 |
| 27(M) | 0.30 | 185 | 181 | 140 | |
| 28(F) | 0.30 | 155 | 150 | 74 | |
| 30(F) | 0.30 | 208 | 163 | 179 | |
| 32(F) | 0.30 | 123 | 115 | 124 | |
| 36(F) | 0.30 | 163 | 165 | 89 | |
| 37(F) | 0.30 | 144 | 149 | 61 | 139 |

M = males; F = females
[a]cholesterol amounts expressed in milligrams per deciliter
[b]measurements taken 4 weeks after GM-CSF dosing stopped

TABLE 2

Human Patient Population 1

| Dose (mg/ml) | Median Maximum Percent Decrease in Cholesterol |
|---|---|
| 0.0005 | 25 |
| 0.001 | 22.5 |
| 0.003 | 0.0 |
| 0.30 | 25 |
| 0.60 | 50 |

TABLE 3

Human Patient Population 2

| Dose (mg/ml) | Median Maximum Percent Decrease in Cholesterol |
|---|---|
| 0.0005 | 8.5 |
| 0.001 | 3.5 |
| 0.003 | 30 |
| 0.010 | 29 |
| 0.015 | 37.5 |
| 0.020 | 34.0 |
| 0.030 | 33.0 |

We claim:

1. A method for lowering the blood serum chloesterol level in a mammal comprising administering to a mammal a serum cholesterol lowering amount of GM-CSF in combination with at least one thrombolytic agent.

2. The method of claim 1 wherein the thrombolytic agent is tissue plasminogen activator, anisoylated plasminogen streptokinase activator complex or streptokinase.

3. A method for lowering the blood serum cholesterol level in a mammal comprising administering to a mammal a serum cholesterol lowering amount of GM-CSF in combination with at least one cholesterol lowering agent selected from the group consisting of lovastatin, gemfibrozil, dilevalol and provastatin.

4. A method for lowering the blood serum cholesterol level in a mammal comprising administering to a mammal a serum cholesterol lowering amount of GM-CSF in combination with at least one other cholesterol lowering agent and one or more thrombolytic agents.

5. The method of claim 4 wherein the thrombolytic agent is tissue plasminogen activator, anisoylated plasminogen streptokinase activator complex or streptokinase.

* * * * *